United States Patent [19]

Helder et al.

[11] 4,036,590
[45] July 19, 1977

[54] METHOD AND APPARATUS FOR THE AUTOMATIC ANALYSIS OF THE CONCENTRATION OF AN INDIVIDUAL COMPONENT OF A FLUID IN A METAL-DEPOSITING BATH HAVING SEVERAL COMPONENTS

[75] Inventors: Johannes Helder, Brugge; Hubert De Steur, Drongen; Marc De Vogelaere, Sint-Kruis, all of Belgium; Wolfgang Pernegger, Erlangen, Germany

[73] Assignee: Siemens Aktiengesellschaft, Berlin & Munich, Germany

[21] Appl. No.: 689,925

[22] Filed: May 25, 1976

[30] Foreign Application Priority Data

June 3, 1975   Germany .............................. 2524611

[51] Int. Cl.$^2$ ...................... G01N 21/24; G01N 33/20
[52] U.S. Cl. .................... 23/230 R; 23/253 R
[58] Field of Search .................. 23/230 R, 253 R, 259

[56] References Cited

U.S. PATENT DOCUMENTS

| | | | |
|---|---|---|---|
| 3,192,968 | 7/1965 | Baruch et al. ...................... | 23/259 X |
| 3,567,389 | 3/1971 | Coulter et al. ...................... | 23/259 X |
| 3,572,998 | 3/1971 | Anthon ............................... | 23/253 R |
| 3,716,338 | 2/1973 | Moran ................................ | 23/253 X |
| 3,764,268 | 10/1973 | Kosowsky .......................... | 23/253 R |

Primary Examiner—R.E. Serwin
Attorney, Agent, or Firm—Hill, Gross, Simpson, Van Santen, Steadman, Chiara & Simpson

[57] ABSTRACT

The invention concerns a method for the automatic analysis and determination of the amount or concentration of a specific component of a fluid in a metal-depositing bath, particularly a gold bath, wherein the fluid has several components. A quantity of bath fluid is taken from the bath in a first step. This quantity of fluid is diluted in a second step, in a third step a reaction agent and a solvent are added to a measured fractional amount of the quantity of diluted fluid during constant stirring, and, in a final step, a quantity of solvent-reaction agent mixture is conveyed to a measuring cuvette of a colorimeter and the concentration of the specific bath component is determined by means of colorimetric measurement. In addition, the invention concerns an apparatus for performing the above described method.

3 Claims, 3 Drawing Figures

METHOD AND APPARATUS FOR THE AUTOMATIC ANALYSIS OF THE CONCENTRATION OF AN INDIVIDUAL COMPONENT OF A FLUID IN A METAL-DEPOSITING BATH HAVING SEVERAL COMPONENTS

BACKGROUND OF THE INVENTION

1. Field of the Invention

This invention relates to a method and apparatus for automatic analysis of the concentration of an individual component of a fluid in a metal depositing bath.

2. Description of the Prior Art

The precise determination of the concentration of individual bath components, particularly in the case of metal-depositing baths, often presents difficulties. Although the material composition of the individual bath is known, the difficulty often arises that the individual components are subjected to great fluctuations in quantity of concentration during the operation of the baths. In the case of baths through which current passes and electrochemical separation of molecules takes place, the baths are warm and the fluid evaporates. Also, the metal concentrations in the baths of this type are dependent upon the quantity of production parts to be coated which are guided through the bath. In the case of gold baths, an attempt is made to keep the gold concentration as close to the nominal value as possible. For the quantitative analysis of gold concentration in a gold bath having other important components such as cobalt, citric acid and organic additions besides the gold in complexed form a colorimetric method of analysis is commonly employed. Such a method is known and includes the use of the dyestuff "Astraviolet", 1-methyl-2-(p-diethylaminostyrene-3,3'dimethylindol) chloride (see Armeanu and Baloui, Anal. Chim. Acta, volume 44, [1969] pages 230 to 232).

A quantity such a 1ml of the bath solution is highly diluted in a first step. A measured fractional quantity such 1ml is then taken from this highly diluted quantity. To this fractional quantity, the Astraviolet, as well as a solvent, such as benzene is added. This solution is then intensively stirred. After a rest period, the phases separate into a heavier water phase and a lighter benzene-Astraviolet-gold phase. It is understood, of course, that the solvent as well as the Astraviolet must be in a specific ratio within the diluted bath fluid so that a precise assessment as to the concentration of the gold contained in the solution is possible during the subsequent colorimetric measurement and interpolation with the aid of a calibration curve.

Instead of Astraviolet, a different reagent such as Malachite green may be used. See the Roumanian Review of Chemistry (1968), vol. 13, pages 1617 to 1621. There, the procedure is similar to that the described above and the extraction solvent used may be ethyl ether or carbon tetrachloride.

The aforementioned methods are well suited for determining the gold content. However, these methods are disadvantageous since they can be carried out only with a considerable expenditure of time and only by highly qualified personnel. In the case of high precision baths, it is desireable to carry out the analyses as often as possible in order to rapidly determine concentration deviations of individual components of the bath fluid from nominal deviations of individual components of the bath fluid from nominal values so that, i.e., the bath can again be revived or corrected by the addition of measured quantities of correction fluid. In the case of gold baths, rapid measurements permit uniform quality of coated parts while minimizing the consumption of precious metal.

SUMMARY OF THE INVENTION

An object of the invention is therefore to automate the above described method for determining the quantity of concentration of a bath component, particularly a gold component whereby the method can be repeated in short time intervals and can be carried out by use of a comparatively small analyzing device which provides a precise analysis.

According to the invention, the bath fluid is pumped to a circulating system located partially outside of the bath. A sample of the fluid is then taken from this circulating system as a first step.

In a second method step, the bath fluid quantity is diluted in at least two stages. A measured fractional quantity is removed from the first dilution stage and further diluted. In a third step, the reaction agent and solvent are added to the measured quantity of highly diluted bath fluid, and, preferably in a repeated cycle, the measuring curvette of the colorimeter is rinsed with the solvent-reagent- mixture prior to carrying out the colormetric measurement. Through these method steps, it is now possible to mechanically provide an analysis previously done by hand and yet with a high degree of precision. The time for carrying out the analysis is greatly reduced such that when the analyses are repeated often, fluctuations in the concentration of the component of a bath can be monitored and kept within narrow limits.

It is important that prior to the beginning of the analysis, the bath fluid is first pumped around in the circulating system for several minutes to insure that the bath fluid taken from the bath and made available for analysis corresponds to the fluid in the bath at the time of measurement. The further the bath is separated from the analyzing device the more important this method step becomes.

By carrying out the dilution (a dilution of $1:3 \times 10^3$ is preferable) in two stages, a more uniform distribution of the bath fluid in the diluting agent, here, water, is obtained. To mix 1 ml of bath fluid into 3 liters of diluting medium to obtain a uniform distribution is demanding in terms of space and difficulty. If the dilution process is carried out in several stages, however, such as first taking 1 ml of the bath fluid and diluting it with 99 ml of distilled water, stirring this mixture and then again taking 1 ml and diluting with distilled water, a much more uniform distribution of the fluid in the diluting agent is obtained over a shorter treatment period and within a small area.

Repeated rinsing of the colorimeter cuvette serves to wet the transparent walls of the cuvette and to eliminate solvent vapor from the cuvette interior prior to carrying out the colorimetric measurement.

Thus, the foregoing method steps serve the common purpose of increasing the measuring accuracy and of automating the known methodology, which, until the present time, could only be carried out manually.

It is an additional object of the invention to produce an automatically operating analysis device for the quantitative determination of concentration for an individual component contained in a fluid. The apparatus consists of three stationary receptacles: a receiving receptacle for the bath fluid which is to be analyzed; a diluting receptacle for the fluid which is to be analyzed; and a reaction receptacle for receiving the diluted fluid with the reaction agent and the organic solvent. First and second pipettes are arranged over two of the receptacles, respectively. Each pipette connects with a piston pump. The pipettes are mounted to a common automatically operable support holder. In one position of the holder, the first pipette is arranged over the receiving receptacle and the second pipette over the diluting receptacle. In an alternate position of the support holder, the first pipette is arranged over the diluting receptacle and the second pipette over the reaction receptacle. In both positions of the support holder, the mouths of the pipettes dip into the receptacles.

Both pipettes are connected to piston pumps through shift or change-over valves. When one of the pipettes is actuated by a control device through the pistons and shift valves, it moves a measured quantity of fluid from one receptacle and deposits in one of the other receptacles a quantity which has been greatly increased by the diluting agent, preferably distilled water. For example, the device functions such that the first pipette removes 0.5 ml of bath fluid from the receiving receptacle. This pipette is conveyed over the adjacent diluting receptacle by means of the support holder and discharges the quantity of bath fluid plus 10 ml of the diluting agent. This diluting agent may be delivered by means of several loading and expulsion strokes of the piston pump. For example, five piston strokes provide 50 ml of diluting agent to 0.5 ml of bath fluid. Stirring devices in the receptacles thoroughly mix the fluid. After returning the support holder to its original position, the second pipette takes 0.5 ml of diluted bath fluid from the diluting receptacle and expels this quantity, in addition to 10 ml of diluting agent, into the reaction receptacle. After repeated stirring, precisely measured quantities of solvent and reaction agent are introduced into the reaction receptacle. In the case of gold baths, preferably benzene and Astraviolet are used as the solvent and reaction agent. This mixture is again stirred for several minutes such that after a rest period of a few minutes the phases become separated into well defined height positions according to their relative weight. The lighter solvent-reaction phase is automatically suctioned into a cuvette portion of a colorimeter by means of a piston pump, and, after a short duration is again discharged into the reaction receptacle. Shortly thereafter, this operation is repeated once again. Finally, the solution is sucked into the colorimeter cuvette for a subsequent colorimetric measurement. The solution is then discharged into the reaction receptacle, and all receptacles are automatically drained and automatically flushed out with acetone. Acetone has proven to be especially advantegous as a rinsing agent for a gold bath analysis device since it goes into solution with the fluids required for the preparation of the bath fluid for colorimetric measurement.

In terms of operating and safety procedures of the apparatus, it is important that the quantitative additions of the diluting agent as well as the reaction agent are not subject to fluctuations greater than ± 0.5%.

DESCRIPTION OF THE PREFERRED EMBODIMENTS

Figure 1:
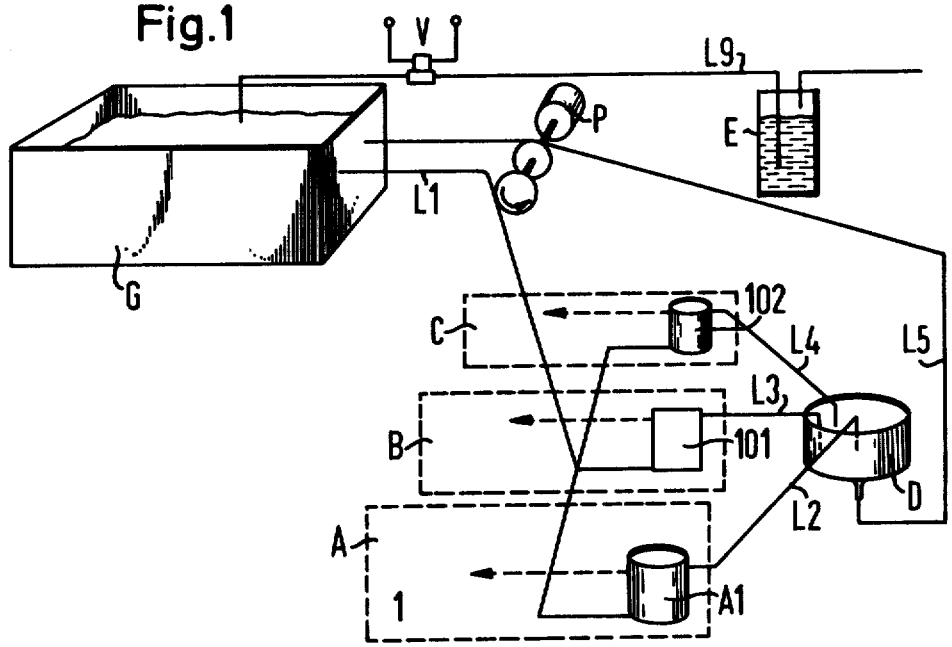
FIG. 1 illustrates the conveyance of bath fluid in an analyzer system.

In FIG. 1, a metal-depositing bath G such as a gold bath is illustrated. This bath is connected via a line L1 to sampling devices A through C. These devices are constructed here as overflow containers, however, they may also be constucted as flowthrough cuvettes or sampling valves and pumps. The devices are connected to a storage container D via overflow lines L2 through L4. A double pump P conveys bath fluid through line L1 and then through sampling devices A through C. Overflowing bath fluid goes into storage container D, and from there back to container G through drain line L5. Devices A through C are each respectively assigned to an analysis section of an analyzer not illustrated here. If G is a gold bath, for example, container A1 functions as the receiving container for the bath fluid of the gold analysis in section 1 which determines the concentration or quantity of the gold component. A valve and a pump 101 are provided for the analysis section which determines cobalt content. A cuvette 102 is assigned to a pH value device C. All analysis sections are connected to a control device, not illustrated here. The control device controls the supply of corrective solution to the bath.

Prior to the beginning of a bath fluid analysis, the double pump P is put in operation. It is important here that pump starting occurs a sufficient length of time prior to the beginning of the analysis, such as at least 2 minutes. Preferably, the double pump is kept in constant operation. This insures that the sampling devices A through C are filled with fresh bath fluid so that the measurement relates to the actual state of the bath fluid at the time of measurement.

Figure 2:
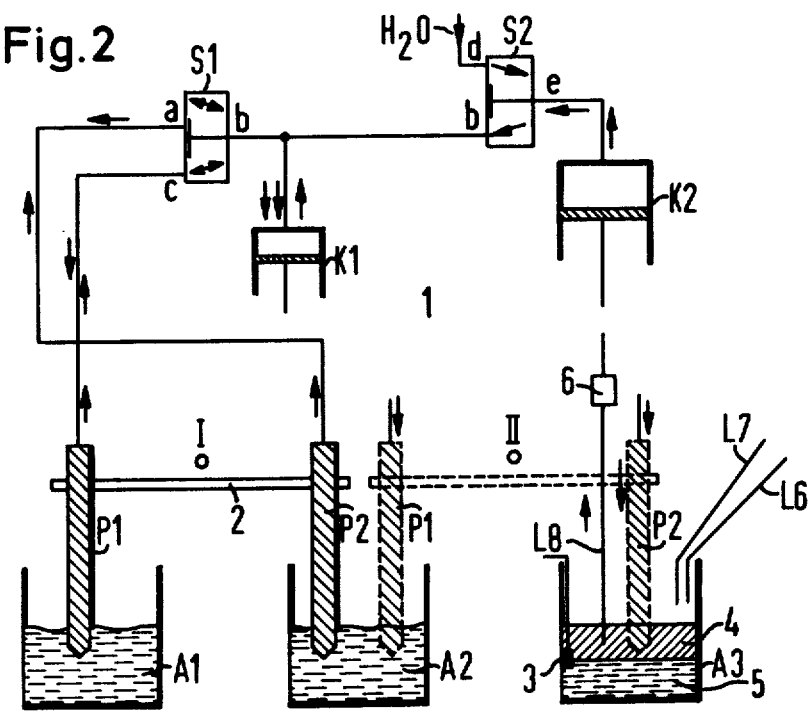
FIG. 2 illustrates the mode of operation of the analyzer of this invention.

FIG. 2 shows a functional diagram of gold analyzer 1 which will serve as a basis for the method explained in detail hereafter. Pipettes P1 and P2 are connected to one another by means of a traverse 2. Containers A1 through A3 of the gold analyzer are well supported on a plate which is not illustrated.

Traverse 2 can be moved from a position I to a position II such that, in position I, pipette P1 dips into container A1, and in position II, dips into container A2. Pipette P2, in position I dips into container A2, and a position II, dips into container A3. Container A1 is the receiving container A as shown in FIG. 1. Container A2 is the so-called diluting container, and container A3 the reaction container.

For a determination of gold content in pure potassium-gold cyanide, the aforementioned photometric method using Astraviolet as explained by Armeanu and Baloiu is employed. In watery solutions, potassium-gold cyanide forms a complex together with Astraviolet. The Astraviolet is then extracted with benzene for the purpose of separating excess dye. The color intensity of the organic phase is dependent upon the gold concentration and may be colorimetrically determined. The precise gold concentration is ascertained by using a straight line calibrator. In the present example, fresh bath fluid is provided in the receiving container A1.

Figure 3:
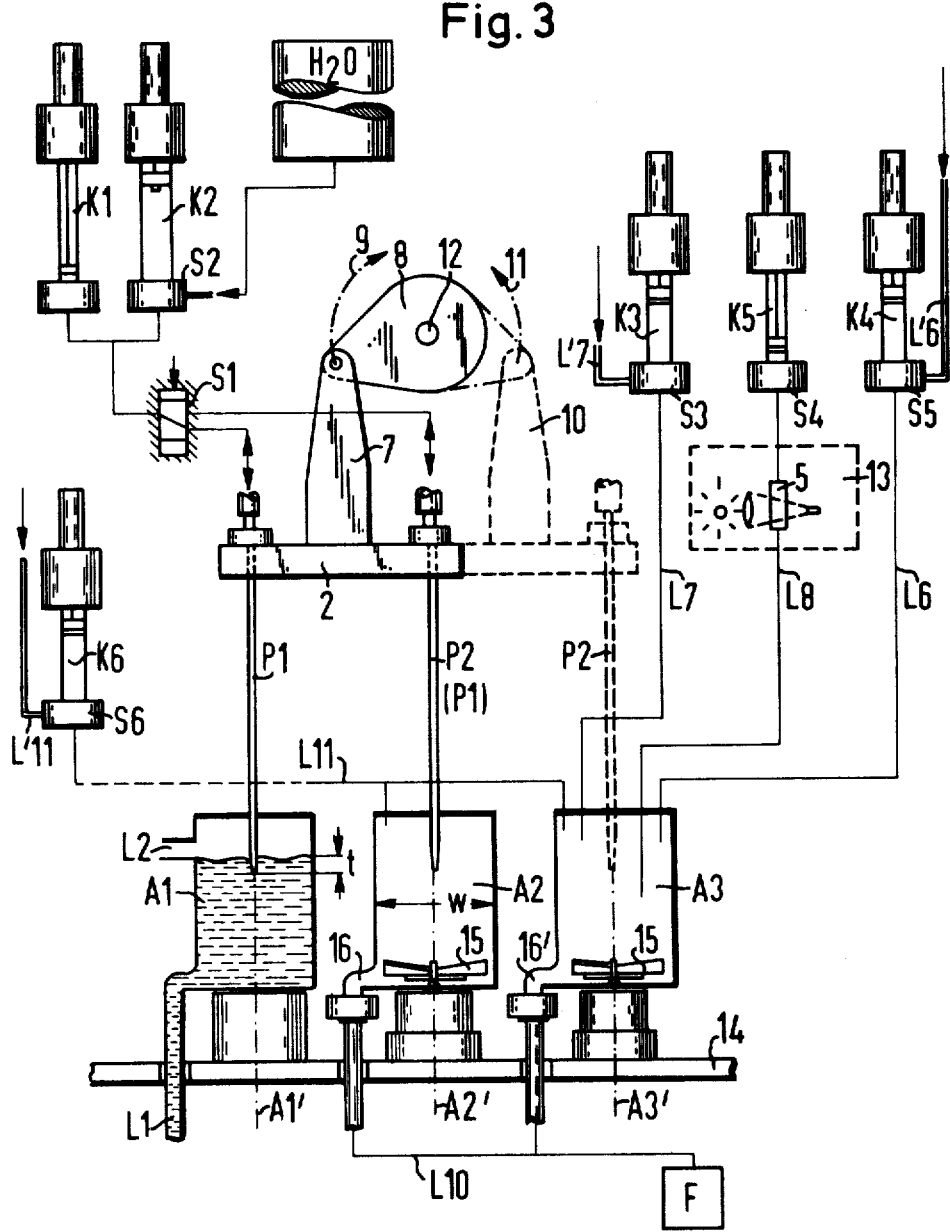
FIG. 3 illustrates a schematic diagram of an analyzer device such as for a gold bath.

The analysis operation is centrally controlled by a program device not illustrated here. Bath fluid, for example, 0.5 ml, is removed by means of first pipette P1 with the aid of a pnuematically operated piston pump K1 via a shift valve S1. For this function, the shift valve S1 is in the position b–c. Both pipettes P1 and P2, as well as all connecting lines, are filled with distilled water. Upon activating the piston pump K1 and immersing the mouth of the pipette into removal receptacle A1, a quantity of bath fluid corresponding to the increase in volume of the piston pump is drawn into the pipette. Traverse 2 holding pipettes P1 and P2 is placed into position II by the control device and the bath sample contained in pipette 1 is expelled into dilution receptacle A2. In order to avoid errors in dosage and to rinse clean the pipette, the water for dilution is added by means of pipette P1. Piston pump K2 serves this purpose. The filling of piston pump K2 occurs via shift valve S2 in position d–e. With a stroke of the piston of piston pump K2, 10 ml of distilled water is sucked up by the pump. Through the control device, valve S2 is then shifted, i.e., shift valve S2 to the position e–b, and valve S1 remains in the position b–c. The shifting of valve S2 to a filling stroke and a discharge stroke takes place automatically six times, so that the bath sample of 0.5 ml together with .60ml of distilled water flows into the diluting receptacle A2. The mixture in dilution receptacle A2 is subsequently stirred by a magnetic stirrer (FIG. 3). During this period, the traverse 2 is returned to position 1 at the command of the control device. Subsequently, valve S1 shifts to position a–b. Pipette P2 is again dipped into the dilution receptacle. By activating piston pump K1, a 0.5 ml diluted bath sample is removed by pipette P2, whereupon the traverse moves to position II. An additional filling stroke and discharge stroke of piston pump K2 occurs, so than now 10 ml of water flows into reaction receptacle A3 via pipette P2. In reaction receptacle A3, the previously diluted bath sample together with 10 ml of water are located, and, through stirring, a second dilution takes place. Via line L6, a measured quantity of Astraviolet solution, and via line L7, a precisely measured quantity of solvent, preferably benzene, are discharged into the reaction receptacle. This misture is stirred for 5 minutes. The Astraviolet-gold cycanide-complex is thereby transferred into the benzene phase.

The extraction of the benzene phase is dependent upon the temperature. A temperature sensor is therefor arranged on the reaction receptacle.

In order to separate the lighter benzene phase 4 from water phase 5, a rest period of approximately 3 minutes is maintained. A small quantity of the upper benzene phase 4, colored by the Astraviolet, is subsequently suctioned into a measuring cuvette 6 of a colorimeter via a line L8 and the absorption is measured in known fashion. The amount of absorption directly relates to the gold component concentration contained in the bath fluid being measured in the present example.

A sample embodiment of an analysis device operating according to the above described method is illustrated in FIG. 3. The traverse 2 positions pipettes P1 and P2 in one position over receptacles A1 and A2, and in the other position over receptacles A2 and A3. The traverse 2 is connected to a support structure 7 which is joined to a movable mounting 8. If the movable mounting is swung from the position illustrated by the solid line in the direction of arrow 9 into the position illustrated by a broken line, pipettes P1 and P2 are thereby raised and transferred from the positions shown by solid lines to the positions shown by broken lines. The pipettes return to the original position in the direction of arrow 11. Movable mounting 8 is connected to a servomotor, not illustrated here, at shaft 12, the regulating and switching operations of the servo-motor taking place by the control device of the analyzer, not shown. The arrangement of pipettes P1 and P2, as well as the measurement of diameter w of diluting receptacle A2, is effected such that the mouth of the pipette dips into the fluid only to a depth t of approximately 5 mm. Such a depth prevents the adhesion of sample fluid to the outer wall of the pipette and avoids the transfer of sample fluid to the adjacent receptacle. Therefore, erroneous measurements are prevented.

As shown in FIG. 3, piston pumps K3 to K5 are connected with lines L6 through L8, respectively. These pumps are constructed in the same manner as pumps K1 or K2. Thus, pump K4 is connected to a reaction agent storage container (not shown) via a line L6' which, in the case of a gold bath analyzer, corresponds to a receptacle containing the Astraviolet. Shift valve S5, in one position, connects the reaction agent storage container to the interior of piston K4 such that, during the intake stroke of the piston, the piston interior is filled with Astraviolet solution. If the valve is decanted by means of the control device, the piston interior is then connected to the reaction container A3 via line L6. Piston K3 is also constructed in corresponding fashion and has a line L7' connected to the storage receptacle containing the solvent.

Supplementing the operational description of the device as specified in FIG. 2, after the separation of the lighter benzene phase from the water phase, a first rinsing stroke takes place. Measuring fluid is thereby drawn up into the measuring cuvette and then, during the return stroke of the piston, is expelled by piston K5 to rinse the cuvette. After a short time, another rinsing stroke as described above takes place. After repeated separation of the phases in the reaction container A3, a measuring stroke of the piston K5 finally occurs. This method step serves to rinse out the cuvette windows.

Through line L8, solvent vapors penetrate the cuvette which coat the cuvette walls and condense there. Through repeated rinsing of the cuvette, the measuring accuracy of the colorimetric measurement is significantly improved. Colorimeter 13 is connected to a regulating device for measured quantities in known fashion. This device controls the supply of corrective fluid to bath G via line L9 (FIG. 1). Line L9 has a control valve V. It is connected to a receptacle E containing a corrective solution. This receptacle is under constant gas pressure. The opening of valve V is controlled by the colorimeter 13, via the regulating device.

Containers A1 through A3 are stabilized on a platform 14. The mutual spacing between the container center axes A1' through A3' corresponds to the spacing between pipette P1 and P3. Motors for magnetic stirring are arranged beneath containers A2 and A3 which cause the stirring blades 15 mounted in the receptacles to rotate. Stirring arrangements of this type are known and are not the subject of this invention.

After an analysis has been made, the control valves and drains 16 and 16' of both containers are opened so that the fluids contained therein are drained off by means of lines L10 and channelled to container F. After the dilution container A2 and the reaction container A3 are drained, these containers are rinsed out with acetone. The process of rinsing takes place via line L11 which is connected to the piston K6. The shift valve S6, in turn, is connected to an acetone storage container via line 11'. Through this arrangement, cleansing of the vessels after a completed analysis occurs and the system is ready for subsequent analyses. Acetone as the rinsing agent has been proven especially advantageous for a gold bath since acetone dissolves all the components which are contained in a cyanide bath, including the reaction agent and solvent in the present case, Astraviolet and benzene.

Although various minor modifications may be suggested by those versed in the art, it should be understood that we wish to employ within the scope of the patent granted hereon all such modifications as reasonably and properly come within the scope of our contribution to the art.

We claim as our invention:

1. A method for the automatic analysis and determination of the magnitude of specific components of a bath fluid having a plurality of components in a metal-depositing bath, comprising the steps of:
   a. pumping the bath fluid for several minutes in a circulation system located partially outside the bath;
   b. taking a sample quantity from the circulation system and diluting the sample quantity in at least first and second dilution operations including the step of,
      i. removing a diluted measured fractional quantity from the first dilution operation and again diluting that fractional quantity in the second dilution operation to create a highly diluted measured quantity;
   c. adding a reaction agent and solvent to the highly diluted measured quantity to create a solvent-reaction agent mixture;
   d. rinsing a measuring cuvette of a colorimeter with the solvent-reaction agent mixture; and
   e. colorimetrically measuring the solvent-reaction agent mixture to determine the magnitude of the specific bath component.

2. The method of claim 1 comprising the further step of rinsing with acetone a reaction vessel in which said solvent-reaction agent mixture is created, and also rinsing with acetone the cuvette of the colorimeter.

3. A method adapted for the automatic analysis of the concentration of specific components of a fluid in a metal-depositing bath comprising the steps of:
   a. pumping the bath fluid for several minutes to a receiving vessel in a circulation system outside the bath;
   b. taking a sample quantity from the receiving vessel and diluting it in a dilution vessel to create a diluted quantity;
   c. taking a quantity from the diluted quantity and diluting it in a reaction vessel to create a highly diluted quantity;
   d. adding a reaction agent and solvent to the highly diluted quantity in the reaction vessel to create a separated mixture containing the reaction agent and solvent;
   e. rinsing a measuring portion of a colorimeter with said mixture; and
   f. colorimetrically measuring said mixture to determine the concentration of a specific bath component.

* * * * *